US011526996B2

(12) United States Patent
Rubinstein et al.

(10) Patent No.: US 11,526,996 B2
(45) Date of Patent: Dec. 13, 2022

(54) ANALYSIS AND VISUALIZATION OF SUBTLE MOTIONS IN VIDEOS

(71) Applicant: GOOGLE LLC, Monntain View, CA (US)

(72) Inventors: Michael Rubinstein, Mountain View, CA (US); Derek Debusschere, Mountain View, CA (US); Mike Krainin, Mountain View, CA (US); Ce Liu, Mountain View, CA (US)

(73) Assignee: Google LLC, Mountain View, CA (US)

( * ) Notice: Subject to any disclaimer, the term of this patent is extended or adjusted under 35 U.S.C. 154(b) by 41 days.

(21) Appl. No.: 17/055,831

(22) PCT Filed: Jun. 20, 2019

(86) PCT No.: PCT/US2019/038111
§ 371 (c)(1),
(2) Date: Nov. 16, 2020

(87) PCT Pub. No.: WO2020/009801
PCT Pub. Date: Jan. 9, 2020

(65) Prior Publication Data
US 2021/0110549 A1    Apr. 15, 2021

Related U.S. Application Data

(60) Provisional application No. 62/692,806, filed on Jul. 1, 2018.

(51) Int. Cl.
*G06K 9/00* (2022.01)
*G06T 7/207* (2017.01)
(Continued)

(52) U.S. Cl.
CPC ........ *G06T 7/207* (2017.01); *A61B 5/02416* (2013.01); *A61B 5/0816* (2013.01);
(Continued)

(58) Field of Classification Search
CPC .......... G06T 7/207; G06T 7/269; G06T 7/73; G06T 2207/10016; G06T 2207/30104;
(Continued)

(56) References Cited

U.S. PATENT DOCUMENTS

| | | | |
|---|---|---|---|
| 6,526,156 B1 * | 2/2003 | Black | G06T 7/251 |
| | | | 382/103 |
| 9,078,009 B2 * | 7/2015 | Bivolarsky | H04N 19/105 |
| 10,709,354 B2 * | 7/2020 | Gunther | A61B 5/0873 |
| 10,776,928 B1 * | 9/2020 | Horvath | G06T 7/246 |

(Continued)

OTHER PUBLICATIONS

He et al ("Video-Based Analysis of Heart Rate Applied to Falls", 2018 IEEE International Symposium on Medical Measurements and Applications (MeMeA), Jun. 2018). (Year: 2018).*

(Continued)

*Primary Examiner* — Shervin K Nakhjavan
(74) *Attorney, Agent, or Firm* — McDonnell Boehnen Hulbert & Berghoff LLP

(57) ABSTRACT

Example embodiments allow for fast, efficient motion-magnification of video streams by decomposing image frames of the video stream into local phase information at multiple spatial scales and/or orientations. The phase information for each image frame is then scaled to magnify local motion and the scaled phase information is transformed back into image frames to generate a motion-magnified video stream. Scaling of the phase information can include temporal filtering of the phase information across image frames, for example, to magnify motion at a particular frequency. In some embodiments, temporal filtering of phase information at a frequency of breathing, cardiovascular pulse, or some other process of interest allows for motion-magnification of motions within the video stream corresponding to the breathing or the other particular process of interest. The phase information can also be used to determine time-
(Continued)

varying motion signals corresponding to motions of interest within the video stream.

18 Claims, 7 Drawing Sheets

(51) Int. Cl.
    *G06T 7/269* (2017.01)
    *G06T 7/73* (2017.01)
    *A61B 5/024* (2006.01)
    *A61B 5/08* (2006.01)

(52) U.S. Cl.
    CPC ............... *G06T 7/269* (2017.01); *G06T 7/73* (2017.01); *G06T 2207/10016* (2013.01); *G06T 2207/30104* (2013.01)

(58) Field of Classification Search
    CPC ...... G06T 2207/30101; A61B 5/02416; A61B 5/0816
    See application file for complete search history.

(56) References Cited

U.S. PATENT DOCUMENTS

| | | | | |
|---|---|---|---|---|
| 2012/0050334 | A1* | 3/2012 | Velthoven | G06T 7/44 345/660 |
| 2014/0044368 | A1* | 2/2014 | Tanner | G06T 7/207 382/236 |
| 2020/0229775 | A1* | 7/2020 | Gunther | G06T 7/194 |

OTHER PUBLICATIONS

He et al ("Using Eulerian Video Magnification Framework to Measure Pulse Transit Time", 2014 IEEE International Symposium on Medical Measurements and Applications (MeMeA), Jun. 2014). (Year: 2014).*
Bennett et al ("Adaptive Eulerian Video Processing of Thermal Video: An Experimental Analysis", IEEE Transactions on Instrumentation and Measurement, Apr. 2017). (Year: 2017).*
Wu et al ("PCA-based magnification method for revealing small signals in video" Signal, Image and Video Processing vol. 12, pp. 1293-1299 (2018)). (Year: 2018).*
The International Search Report (IDR) with Written Opinion for PCT/US2019/038111 dated Oct. 21, 2019, pp. 1-19.
Kamble, Kranti et al. "A Review: Eulerian Video Motion Magnification" International Journal of Innovative Research in Computer and Communication Engineering (2015), pp. 2384-2390.
Wu, Hao-Yu et al. "Eulerian video magnification for revealing subtle changes in the world" ACM Transactions on Graphics (2012) vol. 31(4), pp. 1-8.
Wadhwa, Neal et al. "Riesz pyramids for fast phase-based video magnification" 2014 IEEE International Conference on Computational Photography (ICCP), IEEE (2014), pp. 1-10.
Yi, Liu et al. "Video motion magnification based on Laplacian-Riesz pyramid" Proceedings of SPIE (2016) vol. 10255, pp. 102553F-102553F.
Joao Ribas: "I could (technically) tell your heartbeat from your Snapchat video" Feb. 4, 2018 (Feb. 4, 2018), XP055611075, Retrieved from the Internet: URL:https://medium.com/@joaoribas/i-can-te chnically-tell-your-heartbeat-from-your-snapchat-video-593c6c11df4c [retrieved on Aug. 6, 2019].

* cited by examiner

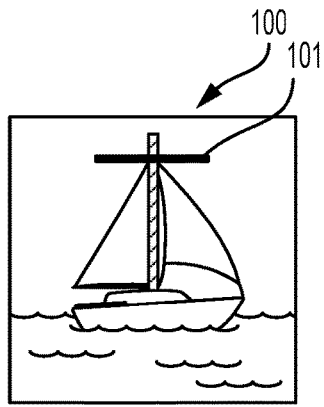
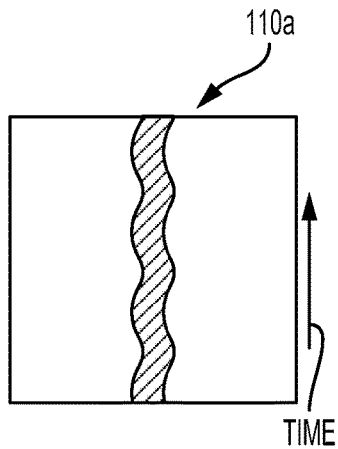
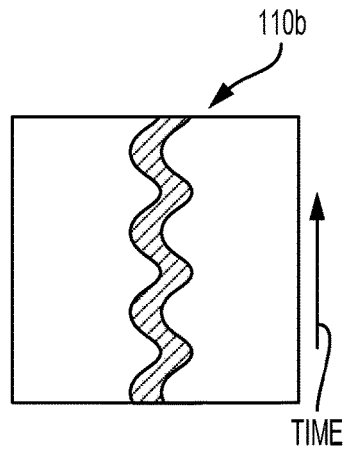
FIG. 1A          FIG. 1B          FIG. 1C
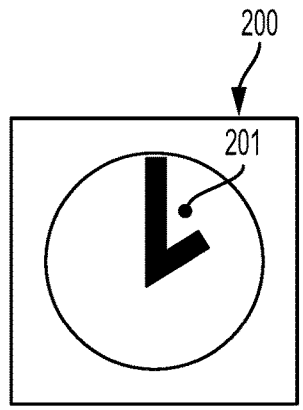
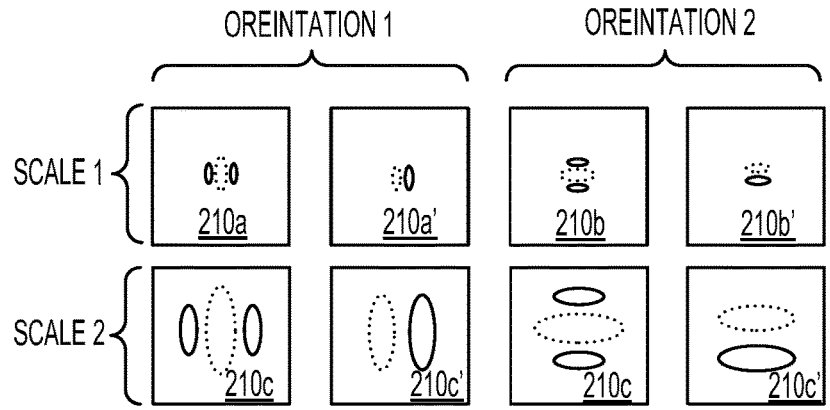
FIG. 2A          FIG. 2B
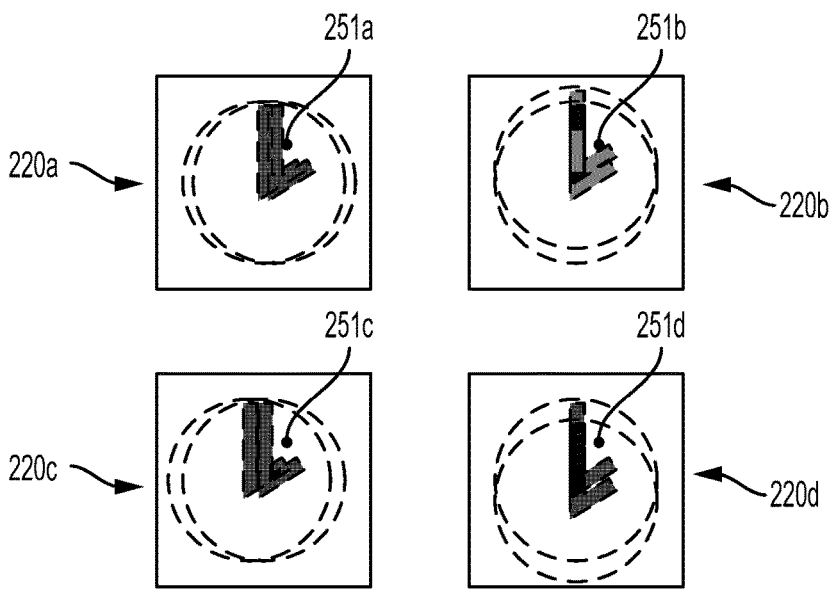
FIG. 2C

ANALYSIS AND VISUALIZATION OF SUBTLE MOTIONS IN VIDEOS

BACKGROUND

It is advantageous in a variety of applications to detect and/or magnify motion that is present in a video. For example, it could be beneficial to magnify motion in a video of a sleeping child in order to verify that the child is breathing and/or to detect a rate of breathing of the child. In order to magnify and/or detect motion in a video, a variety of techniques can be applied. For example, an optical flow map could be determined by comparing different images of the video. Such an optical flow map could then be used to magnify motion within the video, e.g., by distorting the image frames of the video to enhance motion represented in the optical flow map.

One known technique for monitoring the heart rate and cardiac cycle of a person is a plethysmogram, which is a volumetric measurement of an organ such as a subcutaneous vein or artery. An optically obtained plethysmogram is referred to as a photo plethysmogram, and may be obtained using a pulse oximeter which illuminates a person's skin and measures changes in light absorption arising from changes in the blood supply as, with each cardiac cycle, the heart pumps blood to the periphery causing a pressure pulse in the blood system. Even though this pressure pulse is somewhat damped by the time it reaches the skin, it is enough to distend the arteries in the subcutaneous tissue and a pressure pulse can also be seen in some veins. Measuring these pressure pulses provides a measure of the person's heart rate and cardiac cycle.

One application of this technique is in measurements of the jugular venous pressure (JVP), which is the indirectly observed pressure over the venous system. Measurements of JVP can be useful in the differentiation of different forms of heart and lung disease. However, pressure pulses in the JVP are hard to observe. Currently, the only way to obtain a JVP trace is by use of a catheter, which is an invasive technique.

SUMMARY

Motion magnification can be accomplished by transforming images from a video stream to generate local phase information about contents of the images. This phase information can then be scaled, filtered (e.g., temporally filtered across images of the video stream), or otherwise manipulated to emphasize/de-emphasize motion within the video stream. The manipulated phase information can then be transformed back into a set of images to generate a motion-magnified video stream. Steerable image pyramids, Reisz image pyramids, or other transformations can be used to generate the phase information and/or to transform manipulated phase information back into images. Additionally or alternatively, the phase information can be used to generate information about motion within the video stream, e.g., to detect periodic motion related to breathing and/or a cardio-vascular pulse.

An aspect of the present disclosure relates to a method implemented by one or more computers, the method including: (i) generating a first set of image phase information for a first image of a video stream by (1) applying a first set of filters to the first image to generate information about a first local phase of contents of the first image at a first spatial scale, and (2) applying a second set of filters to the first image to generate information about a second local phase of contents of the first image at a second spatial scale, where the first and second spatial scales differ. The method additionally includes (ii) generating a second set of image phase information for a second image of the video stream by (1) applying the first set of filters to the second image to generate information about a first local phase of contents of the second image at the first spatial scale, and (2) applying the second set of filters to the second image to generate information about a second local phase of contents of the second image at the second spatial scale. The method yet further includes (iii) based on the first set of image phase information and the second set of image phase information, generating a first set of modified image phase information and a second set of modified image phase information by (1) applying a temporal filter to the first and second sets of image phase information to determine a first component of the first set of image phase information at a specified temporal frequency and second component of the second set of image phase information at the specified temporal frequency; (2) generating the first set of modified image phase information by scaling by a first scale factor the first component of the first set of image phase information; and (3) generating the second set of modified image phase information by scaling by the first scale factor the second component of the second set of image phase information. The method additionally includes (iv) generating a motion-magnified video stream that includes a first motion-magnified image and a second motion-magnified image. Generating the motion-magnified video stream includes: (1) applying the first and second sets of filters to the first set of modified image phase information to generate the first motion-magnified image; and (2) applying the first and second sets of filters to the second set of modified image phase information to generate the second motion-magnified image.

A method of this aspect generates a motion-magnified video stream, in which the amplitude of motion of an object in the video stream is magnified (that is a "motion-magnified image"), so that the motion of the object is easier to detect in the motion-magnified video stream than it is in the original video stream. Further, the method magnifies the amplitude only of motion at or near a specified frequency. The motion at the specified frequency is therefore easier to detect/observe in the motion-magnified image, as the amplitude of this motion has been selectively increased, relative to motion at other temporal frequencies. If, as an example, the image is of a person and their cardio-vascular pulse rate is known, or can be determined from the video stream, the amplitude of motion at the person's cardio-vascular pulse rate can be magnified in the motion-magnified video stream and so is easier to detect. In one application the method may be used obtain a JVP trace, thereby avoid the need to use a catheter.

Another aspect of the present disclosure relates to a method implemented by one or more computers, the method including: (i) generating a first set of image phase information for a first image of a video stream by (1) applying a first set of filters to the first image to generate information about a first local phase of contents of the first image at a first spatial scale, and (2) applying a second set of filters to the first image to generate information about a second local phase of contents of the first image at a second spatial scale, where the first and second spatial scales differ. The method additionally includes: (ii) generating a second set of image phase information for a second image of the video stream by (1) applying the first set of filters to the second image to generate information about a first local phase of contents of the second image at the first spatial scale, and (2) applying the second set of filters to the second image to generate information about a second local phase of contents of the second image at the second spatial scale; and (iii) based on the first set of image phase information and the second set of image phase information, generating a time-varying motion signal for a particular spatial region within the video stream.

A method of this aspect generates a signal related to motion within a video stream. The method can be modified to provide a motion signal that corresponds only to motion within particular areas of the video stream and/or motion at or within certain temporal frequencies. If, as an example, the video is of a person, the extracted motion signal may be related to their cardio-vascular pulse rate, their jugular venous pressure, their breathing rate, or some other property of interest. In one application the method may be used obtain a JVP trace, thereby avoid the need to use a catheter.

Yet another aspect of the present disclosure relates to a method including: (i) obtaining, by a camera of a device, a video stream that includes first and second images; and (ii) generating, by a controller of the device, a first set of image phase information for the first image by (1) applying a first set of filters to the first image to generate information about a first local phase of contents of the first image at a first spatial scale, and (2) applying a second set of filters to the first image to generate information about a second local phase of contents of the first image at a second spatial scale, where the first and second spatial scales differ. The method additionally includes (iii) generating, by the controller, a second set of image phase information for the second image by (1) applying the first set of filters to the second image to generate information about a first local phase of contents of the second image at the first spatial scale, and (2) applying the second set of filters to the second image to generate information about a second local phase of contents of the second image at the second spatial scale. The method yet further includes: (iv) scaling, by the controller, the first set of image phase information and the second set of image phase information to generate a first set of modified image phase information and a second set of modified image phase information, respectively; (v) transmitting, from a transmitter of the device, an indication of the video stream; and (vi) transmitting, from the transmitter, an indication of the first and second sets of modified image phase information.

A method of this aspect advantageously generates a signal related to motion within a video stream and transmits this motion signal along with the video stream itself. A receiving device (e.g., a cellphone, a computer) could then use the motion signal to distort the video stream, generating a motion-magnified video stream. This segregation of computational tasks suits a situation wherein video transmission bandwidth is constrained by performing the motion-signal generation in the same device that generates the video stream. The video stream and/or motion signal can then be compressed before transmission, reducing video transmission bandwidth requirements.

For the avoidance of doubt, the term "first image" is used to denote a particular image of the video stream and does not require that the "first image" is the initial image" of the video stream.

The first image and the second image are not required to be consecutive images in the video stream, although they may be consecutive images.

The video stream may further comprise a plurality of additional images, and the method may further comprise applying the first and second sets of filters to each of the images in the plurality of additional images to generate additional image phase information for the plurality of additional images. The additional image phase information may then be used to generate one or more additional motion-magnified images in the motion-magnified video stream, in the same manner as defined for the first and second sets of image phase information.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE FIGURES

FIG. 1A depicts contents of an example image of a video stream.

FIG. 1B depicts variation within a portion of the video stream depicted in FIG. 1A.

FIG. 1C depicts variation within a motion-magnified version of the portion of the video stream depicted in FIG. 1B.

FIG. 2A depicts contents of an example image.

FIG. 2B depicts two sets of image filters.

FIG. 2C depicts version of the example image of FIG. 2A after having been filtered by the filters depicted in FIG. 2B

DETAILED DESCRIPTION

Figure 3A:
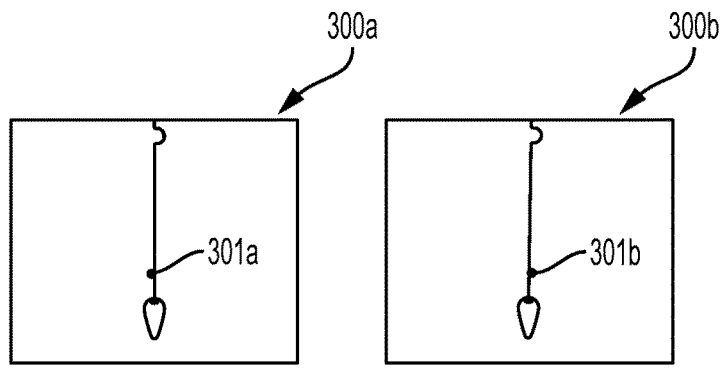
FIG. 3A depicts contents of example images of a video stream.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. Overview

It is beneficial in a variety of applications to magnify (or diminish) motions, in particular small-amplitude motions, that are present in video. For example, the subtle motion of a child's breathing or other movements, present in a video stream provided by a baby monitor, could be magnified to facilitate a parent or caregiver confirming that the child is breathing normally. In another example, the small motions of skin, due to the motion of blood in blood vessels beneath the skin, could be magnified in order to detect a pulse rate or to provide some other medical diagnostic information about a person who is present in a video. Additionally, methods to perform such motion magnification could also provide signals related to the motion that is present in a video. For example, a motion signal relating to the motion of skin over a blood vessel could be generated and used to determine a pulse rate, to estimate a photoplethysmographic signal, to determine a blood pressure, or to determine some other health information about a person.

Such motion magnification and/or detection can be achieved in a variety of ways. For example, methods for optical flow detection could be used to detect the motion of contents of a video stream from frame to frame within the video, and this detected motion could then be magnified to generate a motion-magnified video stream, could be quantified to detect breathing or other motion within the video, or could be used for some other application. Additionally or alternatively, filtering or other transformation methods could be used to efficiently determine the local spatial phase within each frame of the video stream. Such local phase information is analogous to the phase of components of a Fourier or similar transformation of the image, but restricted in some manner such that the "local phase" describes such phase information for a restricted, local area within the image.

Such local phase information could be determined across a number of image frames of a video stream and the variation in such local phase information, for a given region within the images of the video stream, could be related to motion that occurs in the given region. Since the local phase information represents the phase of image contents within a prescribed region within an image, the local phase information could be determined at multiple different spatial scales (e.g., using a steerable image pyramid, a Reisz image pyramid, or some other multi-scale image processing technique) in order to detect motion at the different spatial scales. So, the local phase information at a particular location within the images of a video stream, and at a particular spatial scale, could be determined for a sequence of the images of the video stream and used as a proxy for motion at the particular scale and at the particular location within the video stream.

Such a motion-related signal could be related to breathing, a cardiovascular pulse, or some other motion of interest and the motion-related signal could, accordingly, be used to detect and/or analyze such motion (e.g., to detect a presence or rate of breathing, to detect a cardiovascular pulse rate or blood pressure). Additionally or alternatively, such local phase information could be used to locate motion and/or moving objects within the video stream (e.g., to locate a child within a video by determining the portion(s) of the video stream that correspond to local phase information that changes, over time, in a manner corresponding to a breathing rate of the child).

Such generated local phase information could be modified, and the modified phase information transformed back into an image, in order to generate a motion-magnified and/or motion-attenuated video stream. This could include applying a temporal filter or other technique to the phase information, across image frames of the video stream, in order to generate a component of the phase information that is related to the motion of interest to be magnified/attenuated. The frequency or other information specifying the temporal filtering could be determined from the phase information itself, e.g., by extracting a motion signal relating to breathing or other motions of interest within the video stream and determining a breathing rate (or other characteristic) from the motion signal.

In an illustrative example, a bandpass filter with a center frequency corresponding to the breathing rate (measured, estimated, and/or expected) of a person represented in a video stream could be applied to the phase information determined from the images of the video stream. For example, the phase information, across the sequential images of a video stream, for a particular spatial scale and a particular location within the frame of the video stream could be temporally filtered by the bandpass filter to generate a filtered component of the phase information, at the bandpass frequency, for the particular spatial scale and location within the frame of the video stream. This could additionally performed for some or all of the other spatial scales and/or locations of the phase information determined for the video stream. That filtered component could then be multiplied by a greater-than-unity scale factor in order to generate modified phase information. The modified phase information could then be transformed back into images of a motion-magnified video stream, in which motions at or near the bandpass center frequency (e.g., motions related to the person's breathing) are magnified relative to the original video stream. Additionally or alternatively, certain temporal components within the phase information could be scaled by a less-than-unity scale factor, in order to diminish the corresponding motion. For example, a highpass filter could be applied to the phase information for a video stream and the resulting component of the image phase information could be attenuated. The modified phase information could then be transformed back into images of a motion-magnified video stream, in which motions above or near the highpass frequency (e.g., motions related to heat haze in the video stream) are diminished relative to the original video stream.

FIG. 1A shows an example frame 100 of a video stream representing a boat. Over time (i.e., across the image frames of the video stream), the elements of the boat move within the video. For example, the mast of the boat may oscillate back and forth horizontally within the video stream (i.e., "over time" or across the sequential image frames of the video stream). This oscillating motion is illustrated in FIG. 1B. FIG. 1B shows a one-dimensional slice of the video stream, located within the frame of the video stream (e.g., within the frame 100 of FIG. 1A) by the indicator bar 101. The vertical axis of FIG. 1B represents time and/or the index of image frames of the video stream. Thus, as the mast repeatedly moves left and right, the dark portion of the indicated slice of the video stream (representing the portion of the slice occupied by the mast of the boat) moves left and right within FIG. 1B. The methods described herein can be used to efficiently magnify (or attenuate) motion within a video stream. Thus, these methods could be used to magnify all motion, or motion having a characteristic timescale/frequency corresponding to the oscillation of the mast in the video stream represented in FIGS. 1A and 1B. FIG. 1C shows a one-dimensional slice of such a motion-magnified video stream, a location corresponding that of the indicator bar 101 in the original video stream.

II. Example Motion Extraction and Motion Magnification

Information about the change, over time and/or between image frames, of the 'local' phase at a particular location within a video stream can be related to motion of contents of the video stream at the particular location. Such local phase information, for a particular image frame of the video stream, can be compared by analogy to the phase information generated from a Fourier transformation (or similar transform) of the image, but restricted to local regions of the image. Thus, while a Fourier transform will generate a single phase value for the entire image (at a particular spatial frequency), local phase information can be generated at a plurality of locations across the image (e.g., at a specified spatial sampling frequency).

Such local phase information, for a particular location, being "limited" to describing the phase of contents of the image proximate to the particular location can include the local phase information being based solely on a specified subset of the image that is proximate to the particular location. For example, the local phase information could be determined using a limited-support wavelet, filter, function, or other algorithm that only takes into account pixels (or other informational content) of the image that are within a specified region proximate to the particular location. Alternatively, the local phase information may be "limited" by being preferentially weighted toward portions of the image that are proximate to the particular location. Though the effect of distant portions of the image on the local phase information may be non-zero in such examples, the relative impact of such regions on the determined local phase information, relative to the impact of more proximate regions, is low. For example, a Gaussian chirp, a raised cosine filter, a sinc filter, or some other non-limited-support that takes into account pixels (or other informational content) across the entire image may be used to generate the local phase information.

A set of filters may be applied to an image of a video stream in order to generate local phase information for the image. A variety of filter types may be applied, e.g., wavelet filters, raised cosine filters, sinc filters, Gabor filters. Further, the filters applied may include filters sensitive to image information at multiple different scales. For example, the filters used could be part of a set of filters corresponding to an image pyramid, wherein one or more filters of the pyramid correspond, respectively, to different spatial scales. Thus, the output of a filter of such a set of filters will correspond to the phase of features of the image at the respective spatial scale.

FIG. 2A illustrates an example image 200 of a video stream. The image depicts a clock. An example location 201 within the image 200 is indicated. A set of filters (e.g., filters of an image pyramid) could be applied to the image 200 to generate local phase information for the image 200 (e.g., to generate one or more local phase values for the example location 201) at multiple different spatial scales.

FIG. 2B illustrates a set of filters that could be used to generate such local phase information. Each filter shown in FIG. 2B corresponds to a spatial scale and an orientation. Thus, filters 210a and 210a' correspond to a first spatial scale and a first (horizontal) orientation, while filters 210b and 210b' correspond to the same first spatial scale and a second, different (vertical) orientation. Further, filters 210c and 210c' correspond to a second, different spatial scale and the first orientation, while filters 210d and 210d' correspond to the second spatial scale and the second orientation. These example filters are provided as quadrature pairs (e.g., filters 210a and 210a' form a quadrature pair) to permit the determination of both local amplitude and local phase information for an input image (e.g., 200) at multiple different spatial scales and along different orientations.

The filters shown in FIG. 2B can thus be employed to generate local phase and/or amplitude information for the input image 200 at two different spatial scales. This is illustrated in FIG. 2C, which shows a number of examples of the local amplitude information generated by application of different pairs of filters from FIG. 2B to the example image 200. Thus, a first amplitude image 220a could be generated by applying a first pair 210a, 210a' of the filters to the input image 200. Additionally, second 220b, third 220c, and fourth 220d amplitude images could be generated by applying a second 210b, 210b', third 210c, 210c', and fourth 210d, 210d' pair of the filters, respectively, to the input image 200. Similarly, phase images could be generated, at the first and second spatial scales and in the first and second orientations, using the filters (not shown).

Each of the filtered amplitude images 220a, 220b, 220c, 220d or phase images (not shown) is composed of a plurality of determined local phases and amplitudes of the input image 200. This, the local amplitude of the first amplitude image 220a at the indicated location 251a within the first amplitude image 220a represents the local amplitude of the input image 200, at the indicated location 201 within the input image 200, at the first spatial scale along the first orientation. Accordingly, the set of amplitude images 220a, 220b, 220c, 220d represent a set of image amplitude information for the input image 200. Correspondingly, a set of phase images determined as described above could represent a set of image phase information for the input image 200.

Such a set of image phase information could be determined for each image of a video stream. The variation of such phase information from image to image of the video stream may be related to motion within the video at spatial scales corresponding to the spatial scales of the applied filter bank. Thus, we may extract information about that motion (e.g., about subtle or otherwise small-amplitude motion within the video stream, about skin motion related to perfusion of blood and/or flow of blood within blood vessels, about breathing) from the variation of this generated image phase information over time/across image frames.

Additionally or alternatively, this phase information may be temporally filtered, scaled, or otherwise modified. This modified image phase information can then be reconstituted into images of a modified video stream. Depending on the modifications imposed on the image phase information, this modified video stream may exhibit motion that is magnified, diminished, or otherwise modified. Such modifications may be keyed to the temporal characteristics of the motion. For example, regular motion occurring at certain temporal frequencies (e.g., a frequency of breathing, a frequency of a heartbeat) could be magnified while other motions (e.g., high-frequency motions corresponding to image artifacts or noise) may be diminished.

Such processes may be referred to as "motion magnification" (where at apparent magnitude of at least some of the motion in a video stream is increased), and a video stream generated, based on a source video stream, using such processes may be referred to as a "motion-magnified video stream." A particular image frame of such a motion-magnified video stream may be referred to as a "motion-magnified image."

FIG. 3A shows two example images 300a, 300b of a video stream. The video stream depicts the oscillating motion of a pendulum within the frame of the video stream. Illustrated locations 301a and 301b, within respective first 300a and second 300b example images, are located at the same illustrative location within the frame of the video stream. The motion of the pendulum from the first image 300a to the second image 300b results in the portion of the string of the pendulum that is proximate to the illustrated location. As a result, the string of the pendulum appears to the left of the illustrated location 301a in the first image 300a and to the right of the illustrated location 301b in the first image 300b.

Figure 3B:
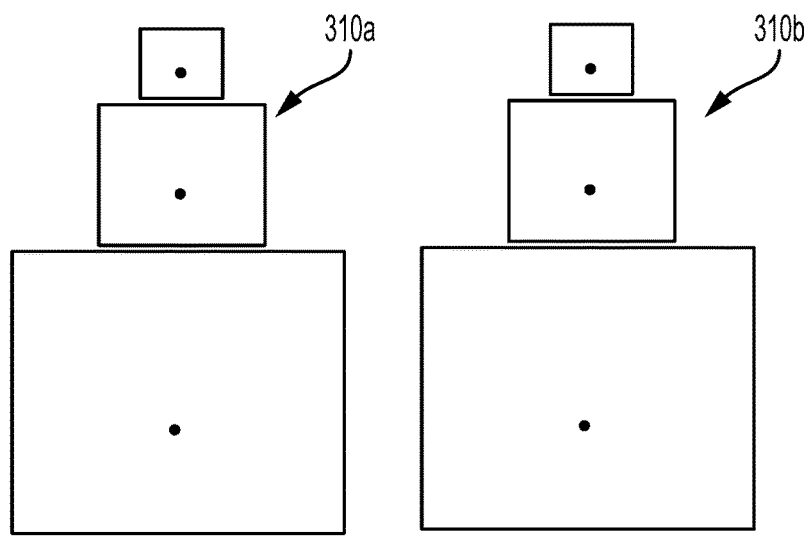
FIG. 3B depicts, schematically, phase information generated from the images depicted in FIG. 3A.

Local phase information may be generated, at multiple different spatial scales, for both of the images 300a, 300b as described above. This is shown in FIG. 3B, which shows a first set of image phase information 310a determined for the first image 300a and a second set of image phase information 310b determined for the second image 300b. Each of the sets of image phase information includes local phase information determined at three different spatial scales (illustrated as three differently-sized squares within the set of image phase information). The dots within the image phase information, at each of the spatial scales, indicate the location, within the set of image phase information, of the local phase information corresponding to the illustrated locations 301a, 301b within the images 300a, 300b of the video stream.

Accordingly, the local phase information at a particular location and spatial scale within the set of image phase information will change, over time and/or across images of an image stream, according to motion of contents of the video stream at the particular location and spatial scale. For example, if the contents of the video stream, at a particular location and spatial scale, move in an oscillatory manner (e.g., as the motion of a pendulum), the local phase information corresponding to the particular spatial scale and location would exhibit an oscillation in time with the oscillation of the pendulum. Such an oscillation could be exhibited in the amplitude, real component, and/or imaginary component of the local phase information, depending on the method employed to generate the local phase information.

Figure 3C:
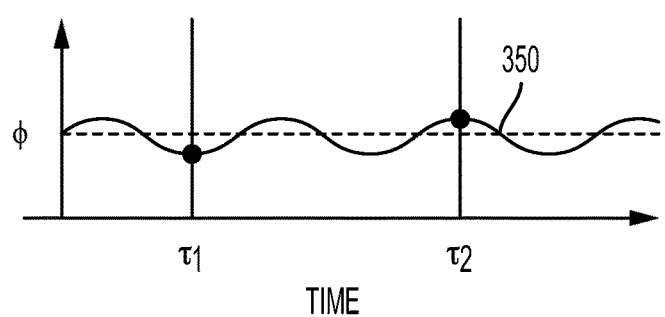
FIG. 3C depicts a time-varying motion signal determined for the video stream depicted in FIG. 3A based on the phase information depicted in FIG. 3B.

This is illustrated by way of illustration in FIG. 3C. FIG. 3C shows the amplitude of the local phase information ("φ") determined, at a particular spatial scale, for the illustrated location 301a, 301b within the video stream represented in FIG. 3A over time and/or across image frames of the video stream ("TIME"). As the pendulum string proximate to the particular location 301a, 301b oscillates horizontally over time, the magnitude of the local phase information determined for the particular location 350 exhibits a sinusoidal variation over time, with an offset (illustrated by the dashed line). The point in time corresponding to the first image 300a is indicated at "$\tau_1$," and the point in time corresponding to the second image 300b is indicated at "$\tau_2$."

This phase information, corresponding to spatial location in an individual image and to motion over time as it varies across the image frames of a video stream, could be used to extract information about the motion or other properties of contents of the video stream. For example, a frequency of variation and/or oscillation of the local phase information corresponding to a particular location within the frame of the video stream could be determined (e.g., by applying a Fourier transform) and used to determine a frequency and/or phase of motion of an object present within the video stream at the particular location. For example, if the object is a person or animal (or a portion thereof), the variation over time of the local phase information could be used to determine a frequency and/or phase of a cardiovascular pulse at one or more locations within a person (e.g., within a portion of subsurface vasculature), a frequency of breathing, or a frequency of some other motion.

Such information about motions within the frame of the video stream could also be used to determine the location, extent, shape, or other information about the moving object within the frame of the video stream. For example, if the video stream depicts a neck of a person or animal, the location of a jugular venous pulse of the person or animal could be determined by determining which areas of the video stream correspond to local image phase information that varies regularly over time at a frequency corresponding to a cardiovascular pulse. Additionally or alternatively, the motion of a particular object, within a particular spatial region within the frame of the video stream, could be determined based on the generated image phase information.

Additionally or alternatively, this phase information could be modified and used to generate modified (e.g., motion-magnified) images for a modified video stream (e.g., by performing the decomposition of the images of the video stream in reverse). For example, the local phase information for each spatial scale and/or location within the video stream could be temporally filtered (e.g., highpassed, bandpassed, lowpassed), scaled, or otherwise modified to magnify certain motions within the video stream and/or to attenuate other motions within the video stream.

This could include applying a temporal filter (e.g., a highpass filter) to the sets of phase information for images of a video stream to determine a component of each of the sets of image phase information that corresponds to the motion to be modified. This filtered component could then be scaled (e.g., increased or decreased in magnitude) and used to generate respective sets of modified image phase information (e.g., by combining the scaled filtered component with other filtered components of the unmodified image phase information).

Such filtering and/or scaling could be applied to all motion within a video stream by, e.g., applying a highpass filter to the sets of image phase information to generate scale-able components of each of the sets of image phase information. Additionally or alternatively, a bandpass filter or other method could be applied to temporally filter the sets of image phase information to generate components of the image phase information at a specified temporal frequency. Such a specified temporal frequency could be a frequency of a motion or process of interest, e.g., a frequency of running or walking, a frequency of breathing, a frequency of a cardiovascular pulse, or some other process of interest. Such a specified frequency could be pre-specified (e.g., according to an expected frequency of a cardiovascular pulse, of breathing, or of some other repeating process) or could be determined at one or more points in time. For example, a frequency of a cardiovascular pulse (or other frequency or process of interest) could be detected using a sensor and/or detected based on image phase information generated as described herein.

Figure 3D:
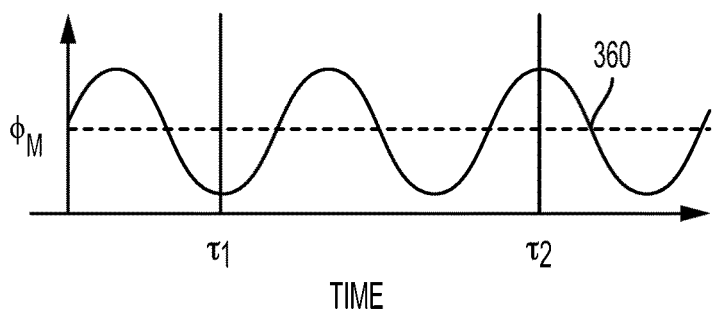
FIG. 3D depicts a magnified version of the time-varying motion signal depicted in FIG. 3C.

An example of such filtering and scaling is illustrated in FIG. 3D. FIG. 3D shows the amplitude of modified local phase information ("$\phi_M$") determined, for the particular spatial scale at the illustrated location 301a, 301b within the video stream, based on the local phase information determined for the particular location 350 represented in FIG. 3B. This modified local phase information determined for the particular location 360 can be determined, e.g., by applying a bandpass or highpass filter to the local phase information determined for the particular location 350 to generate a component of that unmodified local phase information. The generated component could then be scaled (e.g., multiplied by a pre-determined scale factor) and combined with other generated components (e.g., a constant offset corresponding to the dashed-line offset shown in FIG. 3C) to generate sets of modified (e.g., magnified) image phase information. The modified sets of image phase information could then be used to generate respective modified (e.g., motion-magnified) images of a modified video stream.

When magnifying motion in a video stream as described herein, the motion may be magnified by a preset or otherwise-specified amount. For small motions, these methods work to magnify motion with minimal visible artifacts. However, magnification of video streams containing larger motions may result in significant motion-related distortion in the output motion-magnified video stream. The specifics of such distortions may be related to the effective spatial support of the filters used to generate the sets of image phase information from the images of the video stream. Motions having a spatial scale that is greater in extent than the area of support of the filter(s) may result in distortion in the resulting motion-magnified video stream.

In order to prevent the occurrence of such distortion, the degree of scaling (e.g., magnification) applied to the image phase information could be throttled over time based on the magnitude of the motion present in the video stream. For example, the degree of motion magnification could become zero during periods of large-magnitude motion such that the output "motion magnified" video stream is, during the periods of high motion, substantially non-magnified such that distortion is not evident in the output video stream.

In order to determine the degree of motion present in the video stream, the magnitude of image phase variation present over time and/or across image frames of the video stream could be determined based on the sets of image phase information determined for the video stream. This could include determining a magnitude of variation between a temporally-filtered component of a first set of phase information for a first image of the video stream and a temporally-filtered component of a second set of phase information for a second image of the video stream in order to determine an average phase variation for the video stream at a time corresponding to the first and second images of the video stream. Such an average could be determined for the entire frame of the video stream (e.g., based on information about motion across the entirety of each of the first and second images) and applied to determine a scaling factor for modifying the phase information used to generate the entire frame of the output modified (e.g., motion-magnified) video stream. Alternatively, the degree of such a local image phase variation over time could be determined for a plurality of regions within the frame of the video stream and used to throttle the magnitude of the applied motion-magnification correspondingly.

As described above, image phase information can be determined for an image (e.g., an image frame of a video stream) by applying a set of filters to the image. The set of filters can include one or more filters at each of two or more different spatial scales, such that the resulting local phase information represents the local phase of the image at the two or more different spatial scales. A particular filter being "at a particular spatial scale" can include the filter generating an output that is sensitive to spatial information within an input image at the corresponding scale. Accordingly, the spatial scale of a filter could be controlled by adjusting a spatial frequency of a kernel or other component of the filter or by adjusting some other scale-related parameter of the filter. For example, if the filters include a Gabor filter, the spatial scale of each of the filters could be controlled by adjusting the spatial wavelength parameter $\lambda$ of the Gabor filter.

First and second filters sets of filters) differing with respect to spatial scale can include the spatial scale of the filters differing by more than a minimum amount (e.g., by more than 20%) and/or differing by more than a minimum ratio (e.g., 1:1.2) such that the local phase information generated therefrom is sufficiently different to motivate the computational cost of applying both of the filters to and image and performing any additional related processing. The ratio/difference between spatial scales could be specified according to an application, e.g., to provide a desired resolution of spatial scales while minimizing the overall number of filters applied. As a non-limiting list of examples, two spatial scales of corresponding two filters (or sets of filters) could differ with respect to spatial scale by a ratio of 1:1.3, 1:1.414, 1:2, 1:3, 1:4, 1:8, 1:10, 1:16, or some other ratio. The ratio could be specified to simplify computation of the filtered output, e.g., the ratio could be 1:2 or some other power of two to enable re-use of filters and/or filtered outputs in generating local phase information at additional spatial scales.

In embodiments where more than two filters sets of filters) at respectively different spatial scales are used, pairs of neighboring spatial scales could differ by different amounts/ratios or by the same amount/ratio (e.g., forming an exponential series of spatial scales). For example, a first spatial scale could have a ratio of 1:2 with a second spatial scale, while the second spatial scale could, itself, have a ratio of 1:2 with a third spatial scale (thus, the first spatial scale would have a ratio of 1:4 with the third spatial scale).

Filters that correspond to the same spatial scale may differ with respect to one or more properties, so as to provide additional local phase information. For example, a set of filters (e.g., a first set of filters) at a particular spatial scales could each correspond to a respective different spatial orientation. For example, a first filter of such a set could correspond to a horizontal orientation, and thus output local phase information about the phase of spatial variation within an input image along the horizontal direction. A second filter of such a set could correspond to a vertical orientation, and thus output local phase information about the phase of spatial variation within the input image along the vertical direction. In a particular example, such a set of filters could correspond to a steerable image pyramid. The number of filters, and the particular orientation corresponding thereto, could be specified according to an application, e.g., to provide a desired resolution of orientations of local phase information while minimizing the overall number of filters applied.

Other methods and/or filter banks could be used to generate image phase information for an input image. For example, the filters applied to the input image could correspond to a Reisz image pyramid. The output of such filters could then be used to generate, for a plurality of locations within the input image, local phase information. Such local phase information could include a magnitude of the variation of spatial contents of the image at a particular spatial scale. Use of the Reisz image pyramid can reduce computation costs (e.g., as compared to using a steerable image pyramid) by permitting the determination of such magnitude along a locally-maximal direction (rather than, as in the steerable image pyramid, applying a plurality of filters to determine the magnitude of spatial variation along a plurality of respective specified orientations).

III. Example Application: Jugular Venous Pressure

The jugular venous pressure ("JVP") is an important diagnostic sign related to the pressure, over time and space, of blood in the vessels of the neck. The JVP can be used to diagnose and/or indirectly observe a variety of health states or conditions including heart disease, lung disease, heart failure, a variety of disorders of cardiac mis-timing and/or mis-firing, superior vena cava syndrome, tricuspid regurgitation, tricuspid stenosis, constrictive pericarditis, pericardial effusion, or other physiological or anatomical states.

However, the JVP is a very visually subtle sign, from which it can be difficult to detect or to extract diagnostic information. Accordingly, the methods described herein for motion-magnification and/or motion signal extraction by applying filters to generate image phase information can be applied to facilitate the detection and/or use of the JVP. This can include performing motion-magnification to generate a motion-magnified video stream of the neck of a person to be diagnosed. In particular, the image phase information could be temporally filtered to generate local phase components at the detected or otherwise determined cardiovascular pulse frequency of the person in order to preferentially magnify JVP- or otherwise pulse-related motions of the neck. The motion-magnified video stream can then be presented to a physician, who can generate a diagnosis based on the presented video stream.

Additionally or alternatively, automated analysis could be performed on the generated image phase information (e.g., generated local image phase information) to determine a cardiovascular pulse rate, to determine a venous blood pressure waveform, to determine a pressure wave velocity along the neck, or to determine some other useful diagnostic information. This could include detecting the location, within a video stream of the neck of a person and determining the relative phasing or other timing information of the blood pressure and/or blood pulse wave (or other relevant physiological processes) across the neck.

Figure 4A:
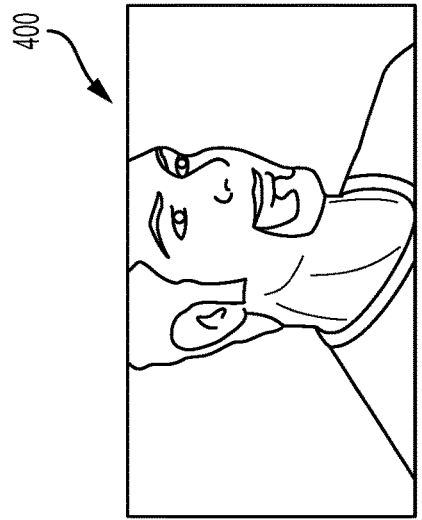
FIG. 4A depicts an image of a video stream that includes a human neck.

FIG. 4A shows an image frame of a video stream that depicts the neck of a person. Such a video stream could be motion-magnified or otherwise processed in order to facilitate the application described herein. This could include detecting the area within the video stream that contains the neck and/or that contains the portion of the neck that is exhibiting motions related to the JVP. Motion magnification could then be performed specifically on the determined area, or other analyses (e.g., pressure wave velocity) could be performed based on the determined area.

The area within the video stream that contains the neck and/or that contains the portion of the neck that is exhibiting motions related to the JVP could be determined by a variety of methods. In some examples, an artificial neural network (e.g., a convolutional neural network) could be used to segment the video stream and/or image frames thereof in order to determine the neck/JVP area. Additionally or alternatively, image phase information generated from the video stream as described herein could be used to determine regions displaying motion at a frequency of the cardiovascular pulse of the person.

Figure 4B:
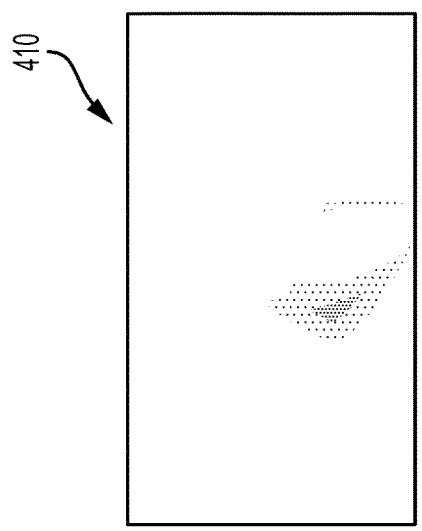
FIG. 4B depicts a magnitude of phase information determined for the video stream depicted in FIG. 4A.
Figure 4C:
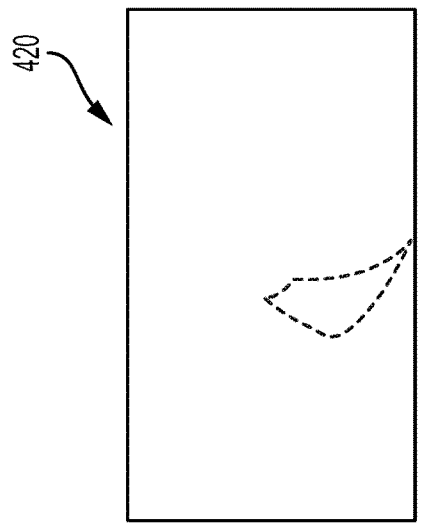
FIG. 4C depicts a location of a jugular venous pulse within the video stream depicted in FIG. 4A.

FIG. 4B shows a "heat map" of motion magnitude within such generated image phase information. Thus, the "heat map" shows increased motion magnitude at the frequency of the cardiovascular pulse at the area, within the video stream, that corresponds to the neck of the person depicted. Such magnitude information could be determined based on a moving average of the local phase magnitude or according to some other method. From this information, a location and extent of the area, within the frame of the video stream, depicting the JVP can be determined. Such a determined area is depicted, by dashed lines, in FIG. 4C.

IV. Example Application: Motion Signal Extraction

The methods described herein, as they generate image phase information for image frames of a video stream, can be used to generate a motion signal that corresponds to motions depicted within the video stream. Such a motion signal can correspond to the motion of a particular spatial region within the video stream, according to the resolution of the local phase information contained within the generated image phase information, or may correspond to the overall motion across the particular spatial region within the video. Such a motion signal could be used to detect a biosignal of interest, e.g., a cardiovascular pulse, a breathing rate, a blood pressure, or some other motion-related physiological variable.

Additionally or alternatively, such a motion signal can be used to facilitate a variety of applications, including affecting the process used to generate the image phase information itself. For example, a magnitude of the motion within the video stream could be used to throttle the degree of motion-magnification applied to the video stream (e.g., by setting a scale factor in order to reduce distortion or other artifacts in the motion-magnified video stream when large-magnitude motions are present). In another example, the motion signal could be used to determine a specified frequency of interest that is used to temporally filter the image phase information before scaling, e.g., to determine a frequency of a cardiovascular pulse in order to preferentially magnify motions within the video stream that occur at that frequency.

Figure 5A:
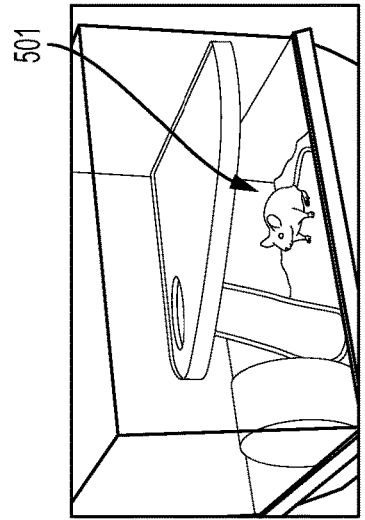
FIG. 5A depicts an image of a video stream that includes a mouse.

A variety of methods could be employed to generate a useful motion signal based on image phase information generated as described herein. To illustrate such methods, FIG. 5A illustrates an image frame of a video stream depicting a mouse 501. The methods described herein could be applied to the video stream in order to generate a motion signal related to breathing of the mouse. The automated, low-cost generation of such a motion signal could be useful, e.g., in generating a large volume of high-temporal-resolution data about the physiological function of the mouse over time in response to a pharmaceutical, surgical, behavioral, and/or genetic intervention or in response to exposure to a pathogen or the onset of some other disease state.

Variation in the local phase information determined, for a particular location within the video stream, across time and/or image frames of the video stream can be related to motion depicted within the video stream at the particular location. Accordingly, if the particular location has been specified (e.g., by determining that the location of the mouse 501 or some other object of interest corresponds to the particular location), a motion signal can be generated based on the local phase information corresponding to the particular location.

Figure 5B:
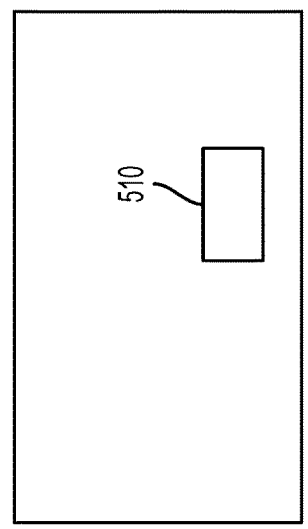
FIG. 5B depicts a region of interest within the video stream depicted in FIG. 5A.

However, determining the motion signal from a single local phase information variable within the image phase information may be susceptible to noise, especially if the location of an object of interest within the frame of the video stream is not precisely and/or accurately known. Alternatively, a particular spatial region corresponding to the object of interest could be determined. This is illustrated by FIG. 5B, which shows a box 510 indicating a particular spatial region within the frame of the video stream that contains the mouse 501. A motion signal for the mouse 501 can then be determined based on the local phase information corresponding to the area within the box 510. This could include determining an average (e.g., an arithmetic average, a geometric average) or some other metric related to the overall phase within the box 510 for each image frame of the video stream.

The location and shape of the box 510, or of some other area within the frame of a video stream (e.g., a circle, an ellipse, and irregularly-shaped area) containing an object of interest, could be determined in a variety of ways. The area could be specified manually. The area could be determined using an artificial neural net (e.g., a convolutional neural net) or some other machine learning algorithm to determine the location and/or extent of an area of interest (e.g., of a region of a neck that is exhibiting a JVP). The area could be determined based on the variation of the image phase information over time/across image frames, e.g., to correspond to an area within the frame of the video stream that is exhibiting motion at a specified frequency.

Additionally or alternatively, a motion signal could be determined by performing a statistical analysis on the image phase information for the image frames of the video stream. Such a statistical analysis could treat each location and spatial scale for which local phase information is determined as a respective variable. The local phase information determined for a particular spatial scale and location across the image frames of the video stream could represent samples of the variable corresponding to the particular spatial scale and location. Each such variable in the set of image phase information will exhibit variation related to a variety of motion sources (e.g., motion related to breathing of the mouse 501) and to noise. Variables corresponding to the mouse 501, for example, will include more of a component related to the breathing motion of the mouse than will variables corresponding to other regions.

Figure 5C:
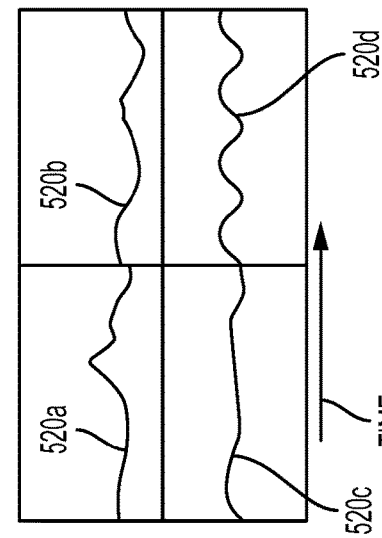
FIG. 5C depicts time-varying motion signals determined from the video stream depicted in FIG. 5A.

A variety of methods could be used to temporally decompose the image phase information to generate one or more motion signals. For example, principal components analysis, independent components analysis, canonical correlation analysis, Fisher's linear discriminant, or some other method of dimensionality reduction or other temporal decomposition method could be used to generate one or more motion signals. Each such method could generate a plurality of time-varying components, each time-varying component corresponding to a source of correlated motion and/or noise across locations within the video stream. This is illustrated in FIG. 5C, which shows first 520a, second 520b, third 520c, and fourth 520d time-varying components generated via temporal decomposition of the image phase information generated for a plurality of image frames of the video stream that depicts the mouse 501. As shown, the fourth time-varying component 520d corresponds to breathing motion of the mouse within the video stream and, accordingly, exhibits periodic variation.

One or more of the generated time-varying components could then be selected and used to generate the desired motion signal. This selection could include determining a noise level, a spectrum, a degree of geographic clustering, a power, or some other property of the time-varying components and/or of their relationship to particular locations within the video stream. For example, selecting the time-varying component corresponding to a cardiovascular pulse, breathing (e.g., of the mouse 501), or some other periodic process could include determining which time-varying component of the set of time-varying components is closest to periodic and/or more periodic than any of the other time-varying components. This could include determining a coherence, a spectrum, a Q-factor, or some other property of the generated time-varying components.

IV. Example Systems

Figure 6:
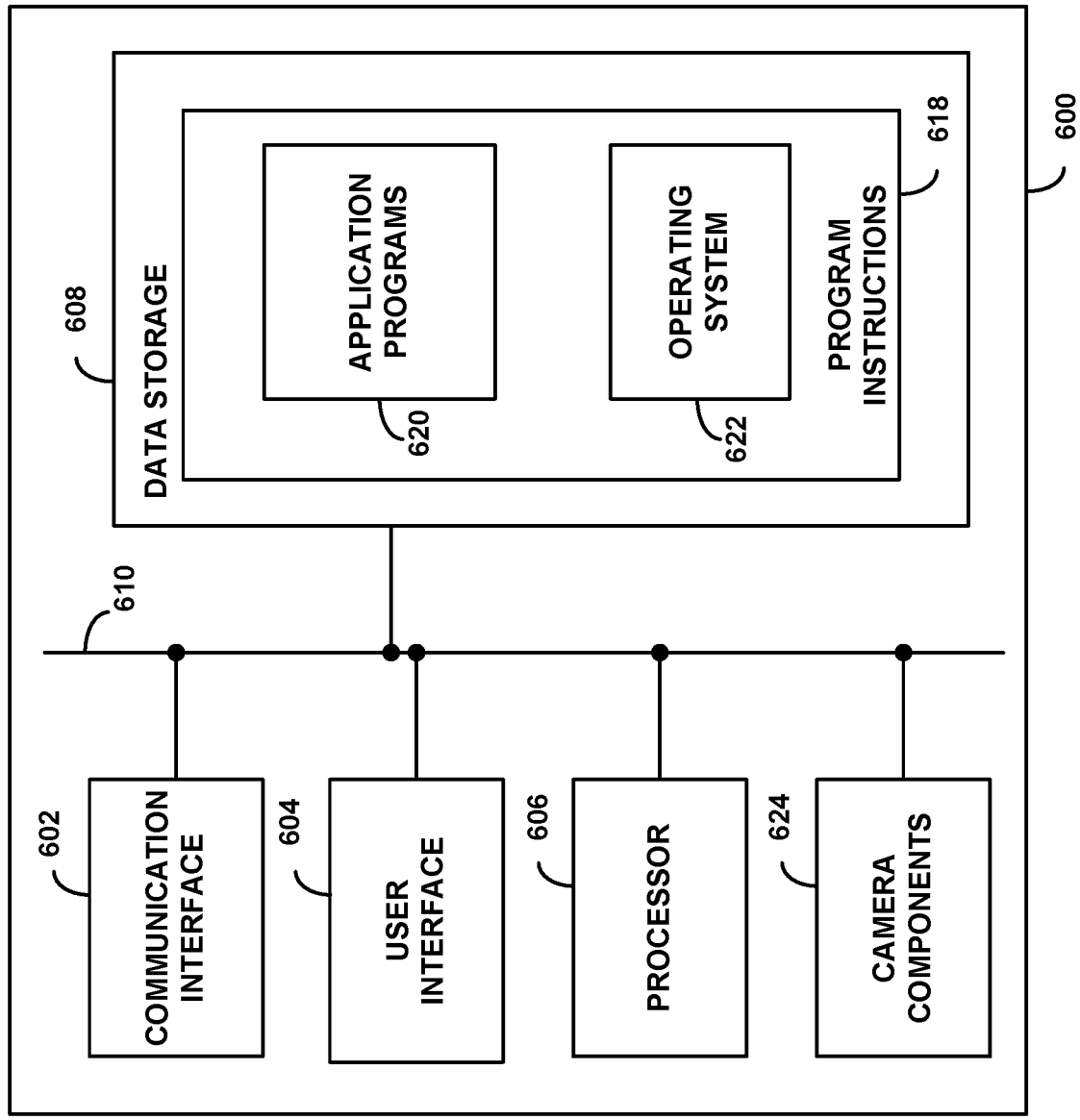
FIG. 6 is a simplified block diagram showing some of the components of an example computing system.

Computational functions (e.g., functions to generate image phase information, to temporally filter local phase information of the image phase information and/or to magnify or attenuate such local phase information, to generate motion-magnified video stream or image frames thereof, to determine motion signals based on image phase information) described herein may be performed by one or more computing systems. Such a computing system may be integrated into or take the form of a computing device, such as a mobile phone, tablet computer, laptop computer, server, home automation element, standalone video capture and processing device, cloud computing network, and/or programmable logic controller. For purposes of example, FIG. 6 is a simplified block diagram showing some of the components of an example computing device 600 that may include camera components 624. Camera components 624 may include one or more cameras, such as visible light cameras, infrared cameras, light field cameras, plenoptic cameras, or other types of cameras.

By way of example and without limitation, computing device 600 may be a cellular mobile telephone (e.g., a smartphone), a still camera, a video camera, a baby monitor, a home security camera, a computer (such as a desktop, notebook, tablet, or handheld computer), a personal digital assistant (PDA), a home automation component, a digital video recorder (DVR), a digital television, a wearable computing device, or some other type of device that may be equipped with at some image capture and/or image processing capabilities. It should be understood that computing device 600 may represent a physical camera device such as a digital camera, a particular physical hardware platform on which a video capture application operates in software, or other combinations of hardware and software that are configured to carry out image capture and/or image processing functions.

As shown in FIG. 6, computing device 600 may include a communication interface 602, a user interface 604, a processor 606, data storage 608, and camera components 624, all of which may be communicatively linked together by a system bus, network, or other connection mechanism 610.

Communication interface 602 may function to allow computing device 600 to communicate, using analog or digital modulation of electric, magnetic, electromagnetic, optical, or other signals, with other devices, access networks, and/or transport networks. Thus, communication interface 602 may facilitate circuit-switched and/or packet-switched communication, such as plain old telephone service (POTS) communication and/or Internet protocol (IP) or other packetized communication. For instance, communication interface 602 may include a chipset and antenna arranged for wireless communication with a radio access network or an access point. Also, communication interface 602 may take the form of or include a wireline interface, such as an Ethernet, Universal Serial Bus (USB), or High-Definition Multimedia Interface (HDMI) port. Communication interface 602 may also take the form of or include a wireless interface, such as a Wifi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 602. Furthermore, communication interface 602 may comprise multiple physical communication interfaces (e.g., a Wifi interface, a BLUETOOTH® interface, and a wide-area wireless interface).

In some embodiments, communication interface 602 may function to allow computing device 600 to communicate, with other devices, remote servers, access networks, and/or transport networks. For example, the communication interface 602 may function to transmit an indication of a video stream (e.g., of a compressed video stream, of a motion-magnified video stream), to transmit an indication of motion within a video stream (e.g., an indication of two or more sets of image phase information determined for image frames of a video stream, an indication of a compressed version thereof, an indication of an optical flow map determined from such image phase information). For example, the computing system 600 could be a cell phone, digital camera, baby monitor, or other image capturing device and the remote system could be a computer, tablet, or cell phone having a display configured to display a motion-magnified video stream.

User interface 604 may function to allow computing device 600 to interact with a user, for example to receive input from and/or to provide output to the user. Thus, user interface 604 may include input components such as a keypad, keyboard, touch-sensitive or presence-sensitive panel, computer mouse, trackball, joystick, microphone, and so on. User interface 604 may also include one or more output components such as a display screen which, for example, may be combined with a presence-sensitive panel. The display screen may be based on CRT, LCD, and/or LED technologies, or other technologies now known or later developed. User interface 604 may also be configured to generate audible output(s), via a speaker, speaker jack, audio output port, audio output device, earphones, and/or other similar devices.

In some embodiments, user interface 604 may include a display that serves to present motion-magnified video streams to a user (e.g., motion-magnified version of video streams generated using the camera components 624). Additionally, user interface 604 may include one or more buttons, switches, knobs, and/or dials that facilitate the configuration and focusing of the camera components 624, the capturing of images and/or video streams using the camera components 624, the generation of motion-magnified video streams therefrom (e.g., to set a scale factor for magnification of motion in the video stream), or to configure some other operation of the system 600. It may be possible that some or all of these buttons, switches, knobs, and/or dials are implemented as functions on a touch- or presence-sensitive panel.

Processor 606 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image alignment, and merging images, among other applications or functions. Data storage 608 may include one or more volatile and/or non-volatile storage components, such as magnetic, optical, flash, or organic storage, and may be integrated in whole or in part with processor 606. Data storage 608 may include removable and/or non-removable components.

Processor 606 may be capable of executing program instructions 618 (e.g., compiled or non-compiled program logic and/or machine code) stored in data storage 608 to carry out the various functions described herein. Therefore, data storage 608 may include a non-transitory computer-readable medium, having stored thereon program instructions that, upon execution by computing device 600, cause computing device 600 to carry out any of the methods, processes, or functions disclosed in this specification and/or the accompanying drawings.

By way of example, program instructions 618 may include an operating system 622 (e.g., an operating system kernel, device driver(s), and/or other modules) and one or more application programs 620 (e.g., camera functions, image filtering, image phase information generation, motion magnification, motion signal generation) installed on computing device 600.

Application programs 620 may take the form of "apps" that could be downloadable to computing device 600 through one or more online application stores or application markets (via, e.g., the communication interface 602). However, application programs can also be installed on computing device 600 in other ways, such as via a web browser or through a physical interface (e.g., a USB port) of the computing device 600.

Camera components 624 may include, but are not limited to, an aperture, shutter, recording surface (e.g., photographic film and/or an image sensor), lens, and/or shutter. Camera components 624 may be controlled at least in part by software executed by processor 606 (e.g., by application programs 620). Further, camera components 624 may include multiple camera systems, which each camera system includes a respective aperture, shutter, recording surface, lens, image sensor, processor, and/or other elements.

In some examples, portions of the methods described herein could be performed by different devices, according to an application. For example, different devices of a system could have different amounts of computational resources (e.g., memory, processor cycles) and different information bandwidths for communication between the devices. For example, a first device could be a small baby monitor or other video camera that could transmit a video stream to another device or server that has the necessary computational resources to perform motion-magnification on the transmitted video stream. Different portions of the methods described herein could be apportioned according to such considerations.

Figure 7:
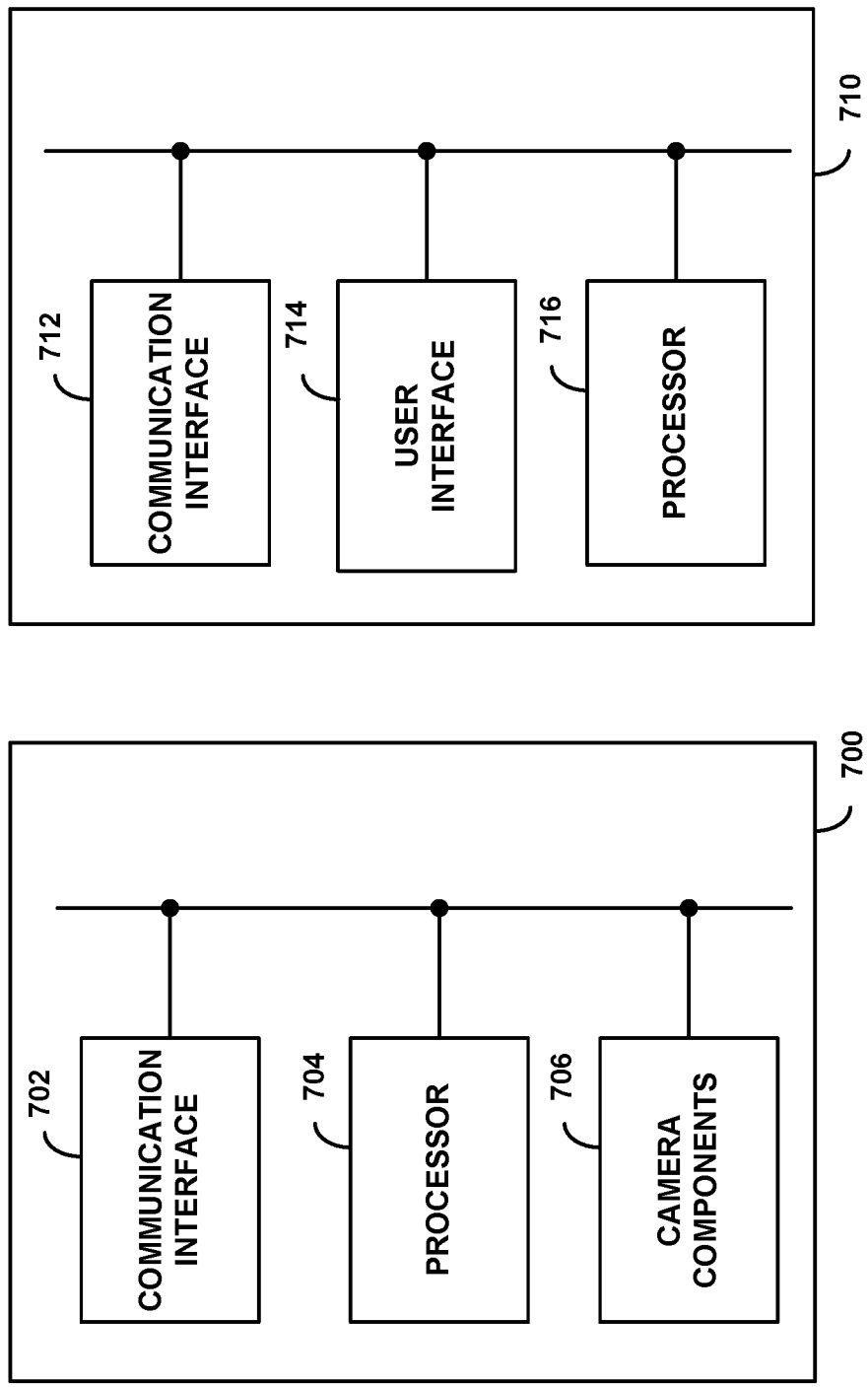
FIG. 7 is a simplified block diagram showing some of the components of an example computing system.

In some examples, the bandwidth available for transmission of a video stream (e.g., between a baby monitor and a cell phone or other display device) may be insufficient to transmit the video stream uncompressed. However, the methods described herein for generation of motion-magnified video streams may be very sensitive to changes in the phase information content of the input video stream. Thus, is can be difficult to perform these methods on an already-compressed video stream. Accordingly, it can be advantageous to have a processor local to a camera (e.g., incorporated into a baby monitor or other apparatus incorporating the camera) perform the image phase information generation and other motion-magnification processes described herein. Information about the video stream and the motion-magnified image phase information can then be transmitted (e.g., in a compressed form) to another device, which can then generate and display a motion-magnified video stream based on the transmitted information, FIG. 7 shows a base station 700 (e.g., a baby monitor, a home security camera, a home automation element) that includes a communication interface 702, a processor 704, and camera components 706. The processor 704 is programmed to operate the camera components 706 to generate a video stream. The processor 704 is also programmed to generate, according to the methods described herein, image phase information for the image frames of the video stream and to generate therefrom motion-magnified image phase information (i.e., image phase information corresponding to a motion-magnified version of image frames of the video stream). The processor 704 is additionally programmed to transmit, via the communication interface 702, an indication of both the video stream and the magnified image phase information.

To preserve power and/or transmission bandwidth, the video stream and/or the magnified image phase information could be compressed before transmission. For the video stream, this could include applying one or more video compression codecs to the video stream to generate a compressed video stream, which could then be transmitted via the communication interface 702. For the magnified image phase information, a generic data compression algorithm could be applied to the magnified video phase information and the compressed data then be transmitted via the communication interface 702. Additionally or alternatively, the magnified image phase information could be used to generate an optical flow map for the video stream. An indication of the optical flow map could then be transmitted via the communication interface 702.

FIG. 7 also shows a receiver unit 710 (e.g., a cell phone, a remote server, a computer, a tablet, a display of a home automation system, a cell phone) that includes a communication interface 712, a processor 716, and a user interface 714. The processor 714 is programmed to operate the communication interface 712 to receive an indication, from the base station 700, of the video stream and the magnified image phase information. The processor 704 is also programmed to operate a display of the user interface 714 to present a motion-magnified video stream. The processor 716 is additionally programmed to generate, based on the received indication of the video stream and the magnified image phase information, such a motion-magnified video stream. This can include applying a codec or other information decompression algorithm to recover an uncompressed version of the video stream and/or magnified image phase information. This can additionally or alternatively include applying optical flow algorithms to distort the received video stream according to the motion represented by the received indication of the magnified image phase information (e.g., represented by an optical flow map provided in such an indication).

V. Example Methods

Figure 8:
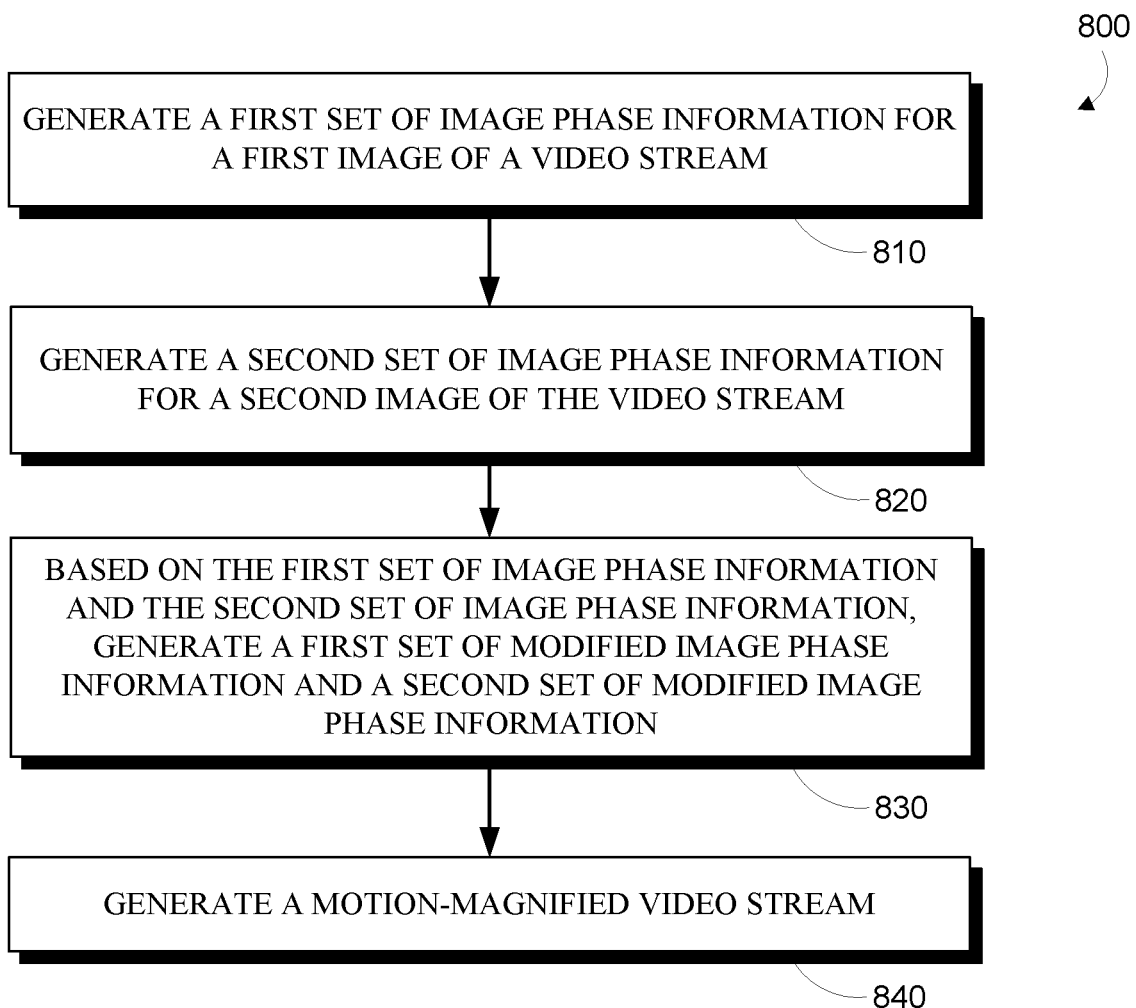
FIG. 8 is a flowchart of a method.

FIG. 8 is a flowchart of a method 800 for generating a motion-magnified video stream. The method 800 includes generating a first set of image phase information for a first image of a video stream (810). This includes (i) applying a first set of filters to the first image to generate information about a first local phase of contents of the first image at a first spatial scale, and (ii) applying a second set of filters to the first image to generate information about a second local phase of contents of the first image at a second spatial scale. The first and second spatial scales differ. The method 800 additionally includes generating a second set of image phase information for a second image of the video stream (820). This includes (i) applying the first set of filters to the second image to generate information about a first local phase of contents of the second image at the first spatial scale, and (ii) applying the second set of filters to the second image to generate information about a second local phase of contents of the second image at the second spatial scale.

The method 800 additionally includes, based on the first set of image phase information and the second set of image phase information, generating a first set of modified image phase information and a second set of modified image phase information (830). This can include applying a highpass filter, a lowpass filter, a bandpass filter, or some other method to temporally filter the first and second sets of image phase information to generate one or more components thereof that correspond to variation, over time, at a specified frequency (e.g., frequency of a cardiovascular pulse). The generated components can then be scaled by a scale factor.

Generating the first set of modified image phase information and the second set of modified image phase information can include (i) applying a temporal filter to the first and second scats of image phase information to determine a first component of the first set of image phase information at a specified temporal frequency and second component of the second set of image phase information at the specified temporal frequency; (ii) generating the first set of modified image phase information by scaling by a first scale factor the first component of the first set of image phase information; and (iii) generating the second set of modified image phase information by scaling by the first scale factor the second component of the second set of image phase information.

The method 800 additionally includes generating a motion-magnified video stream that includes a first motion-magnified image and a second motion-magnified image (840). This can include (i) applying the first and second sets of filters to the first set of modified image phase information to generate the first motion-magnified image; and (ii) applying the first and second sets of filters to the second set of modified image phase information to generate the second motion-magnified image The method 800 could include additional elements or features.

Figure 9:
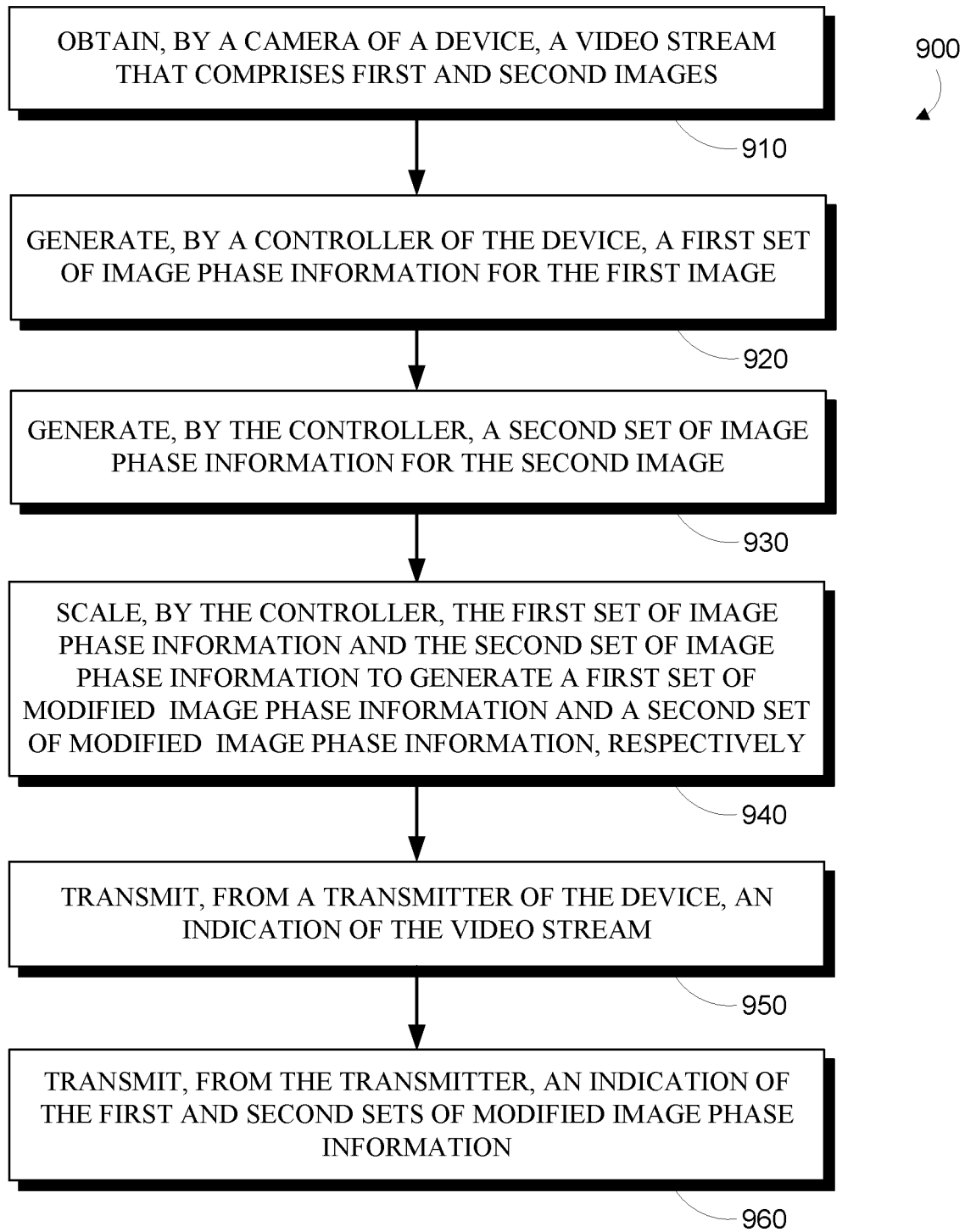
FIG. 9 is a flowchart of a method.

FIG. 9 is a flowchart of a method 900 for generating information related to motion-magnification of a video stream. The method 900 includes obtaining, by a camera of a device, a video stream that comprises first and second images (910). The method 900 additionally includes generating, by a controller of the device, a first set of image phase information for the first image (920). This can include (i) applying a first set of filters to the first image to generate information about a first local phase of contents of the first image at a first spatial scale, and (ii) applying a second set of filters to the first image to generate information about a second local phase of contents of the first image at a second spatial scale. The first and second spatial scales differ The method 900 further includes generating, by the controller, a second set of image phase information for the second image (930). This can include (i) applying the first set of filters to the second image to generate information about a first local phase of contents of the second image at the first spatial scale, and (ii) applying the second set of filters to the second image to generate information about a second local phase of contents of the second image at the second spatial scale.

The method 900 additionally includes scaling, by the controller, the first set of image phase information and the second set of image phase information to generate a first set of modified image phase information and a second set of modified image phase information, respectively (940). The method additionally includes transmitting, from a transmitter of the device, an indication of the video stream (960) and transmitting, from the transmitter, an indication of the first and second sets of modified image phase information (960).

The method 900 could include additional elements or features.

VI. Conclusion

The above detailed description describes various features and functions of disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:

1. A method implemented by one or more computers, the method comprising:

generating a first set of image phase information for a first image of a video stream by (i) applying a first set of filters to the first image to generate information about a first local phase of contents of the first image at a first spatial scale, and (ii) applying a second set of filters to the first image to generate information about a second local phase of contents of the first image at a second spatial scale, wherein the first and second spatial scales differ;

generating a second set of image phase information for a second image of the video stream by (i) applying the first set of filters to the second image to generate information about a first local phase of contents of the second image at the first spatial scale, and (ii) applying the second set of filters to the second image to generate information about a second local phase of contents of the second image at the second spatial scale;

based on the first set of image phase information and the second set of image phase information, generating a first set of modified image phase information and a second set of modified image phase information by (i) applying a temporal filter to the first and second sets of image phase information to determine a first component of the first set of image phase information at a specified temporal frequency and second component of the second set of image phase information at the specified temporal frequency; (ii) generating the first set of modified image phase information by scaling by a first scale factor the first component of the first set of image phase information; and (iii) generating the second set of modified image phase information by scaling by the first scale factor the second component of the second set of image phase information;

determining the location, within the first image, of a jugular venous pulse based on the first component of the first set of image phase information and the second component of the second set of image phase information; and generating a motion-magnified video stream, wherein the motion-magnified video stream comprises a first motion-magnified image and a second motion-magnified image, and wherein generating the motion-magnified video stream comprises:

applying the first and second sets of filters to the first set of modified image phase information to generate the first motion-magnified image; and applying the first and second sets of filters to the second set of modified image phase information to generate the second motion-magnified image.

2. The method of claim 1, wherein the specified temporal frequency corresponds to an expected cardiovascular pulse frequency.

3. The method of claim 1, further comprising:

detecting a frequency of a cardiovascular pulse of a person, wherein the video stream depicts a neck of the person, and wherein the specified temporal frequency corresponds to the detected frequency of the cardiovascular pulse of the person.

4. The method of claim 3, wherein detecting the frequency of the cardiovascular pulse of the person comprises determining the frequency of the cardiovascular pulse of the person based on the first and second sets of image phase information.

5. The method of claim 1, further comprising:
- determining, based on the first component of the first set of image phase information and the second component of the second set of image phase information, an average image phase magnitude; and
- determining, based on the determined average image phase magnitude, the first scale factor.

6. A method implemented by one or more computers, the method comprising:
- generating a first set of image phase information for a first image of a video stream by (i) applying a first set of filters to the first image to generate information about a first local phase of contents of the first image at a first spatial scale, and (ii) applying a second set of filters to the first image to generate information about a second local phase of contents of the first image at a second spatial scale, wherein the first and second spatial scales differ;
- generating a second set of image phase information for a second image of the video stream by (i) applying the first set of filters to the second image to generate information about a first local phase of contents of the second image at the first spatial scale, and (ii) applying the second set of filters to the second image to generate information about a second local phase of contents of the second image at the second spatial scale;
- based on the first set of image phase information and the second set of image phase information, generating a time-varying motion signal for a particular spatial region within the video stream by at least one of:
  - determining a first average image phase based on a portion of the first set of image phase information that corresponds to the particular spatial region within the video stream, and determining a second average image phase based on a portion of the second set of image phase information that corresponds to the particular spatial region within the video stream; or
  - performing a temporal decomposition of a combined set of image phase information by performing at least one of a principal components analysis or an independent components analysis on the combined set of image phase information to determine a set of time-varying components within the set of image phase information, wherein the combined set of image phase information comprises the first set of image phase information and the second set of image phase information.

7. The method of claim 6, wherein generating the time-varying motion signal for a particular spatial region within the video stream comprises (i) determining a first average image phase based on a portion of the first set of image phase information that corresponds to the particular spatial region within the video stream, and (ii) determining a second average image phase based on a portion of the second set of image phase information that corresponds to the particular spatial region within the video stream.

8. The method of claim 6, wherein the video stream further comprises a plurality of additional images, and the method further comprising:
- applying the first and second sets of filters to each of the images in the plurality of additional images to generate additional image phase information for the plurality of additional images;
- wherein generating the time-varying motion signal for a particular spatial region within the video stream comprises performing a temporal decomposition of a combined set of image phase information that comprises the first set of image phase information, the second set of image phase information, and the additional image phase information.

9. The method of claim 8, wherein performing a temporal decomposition of the combined set of image phase information comprises performing at least one of a principal components analysis or an independent components analysis on the combined set of image phase information to determine a set of time-varying components within the set of image phase information.

10. The method of claim 9, further comprising:
- determining which time-varying component of the set of time-varying components is closest to periodic;
- wherein generating the time-varying motion signal for a particular spatial region within the video stream comprises determining the time-varying motion signal based on the set of time-varying components that is closest to periodic.

11. The method of claim 6, further comprising:
- based on the first set of image phase information and the second set of image phase information, generating a first set of modified image phase information and a second set of modified image phase information by (i) applying a temporal filter to the first and second sets of image phase information to determine a first component of the first set of image phase information at a specified temporal frequency and second component of the second set of image phase information at the specified temporal frequency; (ii) generating the first set of modified mage phase information by scaling by a first scale factor the first component of the first set of image phase information; and (iii) generating the second set of modified image phase information by scaling by the first scale factor the second component of the second set of image phase information; and
- generating a motion-magnified video stream, wherein the motion-magnified video stream comprises a first motion-magnified image and a second motion-magnified image, and wherein generating the motion-magnified video stream comprises:
  - applying the first and second sets of filters to the first set of modified image phase information to generate the first motion-magnified image; and
  - applying the first and second sets of filters to the second set of modified image phase information to generate the second motion-magnified image.

12. A method comprising:
- obtaining, by a camera of a device, a video stream, wherein the video stream comprises first and second images;
- generating, by at least one processor of the device, a first set of image phase information for the first image by (i) applying a first set of filters to the first image to generate information about a first local phase of contents of the first image at a first spatial scale, and (ii) applying a second set of filters to the first image to generate information about a second local phase of contents of the first image at a second spatial scale, wherein the first and second spatial scales differ;
- generating, by the at least one processor, a second set of image phase information for the second image by (i) applying the first set of filters to the second image to generate information about a first local phase of contents of the second image at the first spatial scale, and (ii) applying the second set of filters to the second image to generate information about a second local phase of contents of the second image at the second spatial scale;

scaling, by the at least one processor, the first set of image phase information and the second set of image phase information to generate a first set of modified image phase information and a second set of modified image phase information, respectively;

transmitting, from a transmitter of the device, an indication of the video stream; and transmitting, from the transmitter, an indication of the first and second sets of modified image phase information.

13. The method of claim 12, further comprising:

determining a particular spatial region of interest within the video stream;

wherein generating, by the at least one processor of the device, a first set of image phase information for the first image comprises: (i) applying the first set of filters to a portion of the first image that corresponds to the particular spatial region of interest within the video stream to generate information about a first local phase of contents of the first image at the first spatial scale and (ii) applying the second set of filters to the portion of the first image that corresponds to the particular spatial region of interest within the video stream to generate information about a second local phase of contents of the first image at the second spatial scale; and wherein generating, by the at least one processor, a second set of image phase information for the second image comprises: (i) applying the first set of filters to a portion of the second image that corresponds to the particular spatial region of interest within the video stream to generate information about a first local phase of contents of the second image at the first spatial scale and (ii) applying the second set of filters to the portion of the second image that corresponds to the particular spatial region of interest within the video stream to generate information about a second local phase of contents of the second image at the first spatial scale.

14. The method of claim 12, further comprising:

generating, by the at least one processor, a compressed video stream based on the video stream, wherein transmitting an indication of the video stream comprises transmitting an indication of the compressed video stream.

15. The method of claim 12, further comprising:

generating, by the at least one processor, an optical flow map for the video stream based on the first set of modified image phase information and the second set of modified image phase information, wherein transmitting an indication of the first and second sets of modified image phase information comprises transmitting an indication of the optical flow map.

16. The method of claim 12, wherein generating the first and second sets of modified image phase information further comprises:

applying a temporal filter to the first and second sets of image phase information to determine a first component of the first set of image phase information at a specified temporal frequency and second component of the second set of image phase information at the specified temporal frequency;

generating the first set of modified image phase information by scaling by a first scale factor the first component of the first set of image phase information; and generating the second set of modified image phase information by scaling by the first scale factor the second component of the second set of image phase information.

17. The method of claim 16, wherein the specified temporal frequency corresponds to at least one of an expected cardiovascular pulse frequency or an expected breathing frequency.

18. The method of claim 16, further comprising:

detecting, based on the first set of image phase information and the second set of image phase information, a frequency of breathing of a person or animal, wherein the video stream depicts at least a portion of the person or animal, and wherein the specified temporal frequency corresponds to the detected frequency of breathing of the person or animal.

\* \* \* \* \*